United States Patent
Van Bree et al.

(10) Patent No.: US 9,327,020 B2
(45) Date of Patent: May 3, 2016

(54) TRISACCHARIDE DERIVATES, AND THEIR USE AS ADJUVANTS

(75) Inventors: Johannes Gernardus Mathias Marie Van Bree, 's-Hertogenbosch (NL); Everardus Joannes Peter Maria Schenkelaars, '3-Hertogenbosch (NL); Jouwert Anne Turkstra, Dronten (NL); Maria Aldegonda Jacoba Kriek, Lelystad (NL); Robert Patrick Hof, Groningen (NL); Wilhelmus Martinus Maria Schaaper, Almere (NL)

(73) Assignee: Immunovo B.V., 's-Hertogenbosch (NL)

( * ) Notice: Subject to any disclaimer, the term of this patent is extended or adjusted under 35 U.S.C. 154(b) by 0 days.

(21) Appl. No.: 13/703,329

(22) PCT Filed: Jun. 3, 2011

(86) PCT No.: PCT/NL2011/050393
§ 371 (c)(1),
(2), (4) Date: Jul. 2, 2013

(87) PCT Pub. No.: WO2011/155822
PCT Pub. Date: Dec. 15, 2011

(65) Prior Publication Data
US 2013/0273082 A1    Oct. 17, 2013

(30) Foreign Application Priority Data
Jun. 11, 2010    (EP) ..................................... 10165707

(51) Int. Cl.
*A61K 39/39* (2006.01)
*C07H 13/06* (2006.01)
*C07H 1/00* (2006.01)

(52) U.S. Cl.
CPC *A61K 39/39* (2013.01); *C07H 1/00* (2013.01); *C07H 13/06* (2013.01)

(58) Field of Classification Search
None
See application file for complete search history.

(56) References Cited

U.S. PATENT DOCUMENTS

| 4,232,150 | A | 11/1980 | Nair et al. |
| 2009/0042816 | A1 | 2/2009 | Iyer et al. |

FOREIGN PATENT DOCUMENTS

| EP | 1104767 | A1 |   | 6/2001 | | |
| EP | 1792607 | A1 |   | 6/2007 | | |
| JP | 2000169392 | A | * | 6/2000 | ............. | A61K 39/39 |
| WO | WO 88/06143 | A1 |   | 8/1988 | | |
| WO | WO 2009140683 | A1 | * | 11/2009 | ............. | C08G 64/00 |

OTHER PUBLICATIONS

Ogiya et al., JP 2000169392, Jun. 2000, machine translation. Retreived on Jan. 9, 2014 from http://dossier1.ipdl.inpit.go.jp/AIPN/odse_top_dn.ipdl?N0000=7400.*
Definition of "compound" and "composition" in Grant and Hackh's chemical dictionary, 5th Ed. McGraw Hill. 1987.p. 148. ISBN 0-07-024067-1.*
Takeo, K. I., & Kuge, T. (1976). Synthesis of 1, 6-anhydro-1 (6)-thio-β-maltotriose. Carbohydrate Research, 48(2), 282-289.*
Thompson, A., & Wolfrom, M. L. (1952). The Structure of Maltotriose1. Journal of the American Chemical Society, 74(14), 3612-3614.*
Akoh, et al., "One Stage Synthesis of Raffinose Fatty Acid Polyesters", Journal of Food Science, vol. 52, No. 6, pp. 1570-1576 (1987).
Arndt, et al., "Preparation of cellulose oligomers from cellulose triacetate (standard procedure)", Cellulose, Kluwer Academic Publishers, DO, vol. 12, No. 3, pp. 317-326 (2005).
Mogemark, et al., "Influence of saccharide size on the cellular immune response to glycopeptides", Organic & Biomolecular Chemistry, vol. 1, pp. 2063-2069 (2003).
Yao, et al., "Chemoenzymatic Synthesis of iGb3 and Gb3", Organic Letters, vol. 8, No. 6, pp. 911-914 (2006).

* cited by examiner

*Primary Examiner* — Eric Olson
*Assistant Examiner* — Dale R Miller
(74) *Attorney, Agent, or Firm* — Bret E. Field; Makoto Tsunozaki; Bozicevic, Field & Francis LLP

(57) ABSTRACT

The present invention relates to the use of trisaccharide derivates comprising a substituted trisaccharide core, which trisaccharide core is fully substituted with fatty acid ester groups, and optionally one or more anionic groups as adjuvants, to the trisaccharide derivates as such, to a method for preparing such trisaccharides, to trisaccharides obtained with such method, to adjuvant compositions comprising such trisaccharide derivates and to a vaccine or kit comprising such adjuvant compositions.

20 Claims, 7 Drawing Sheets

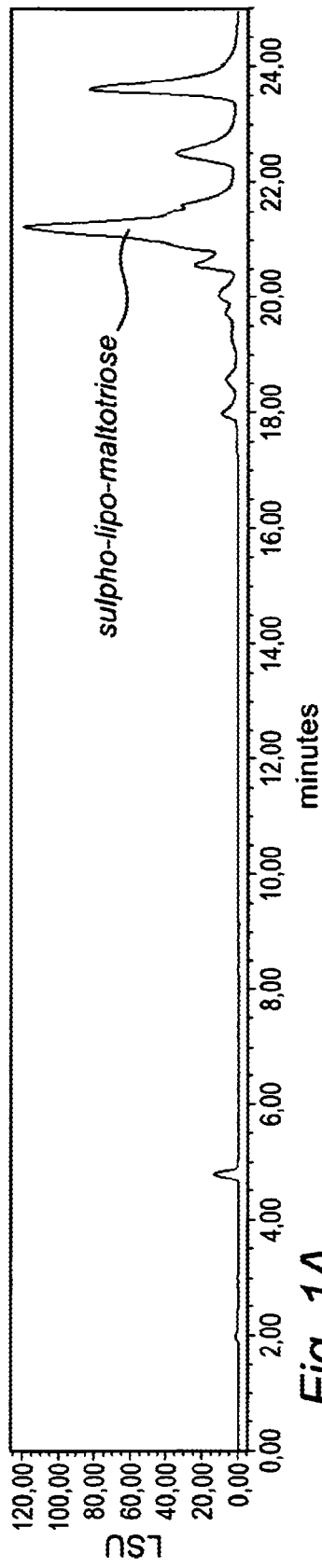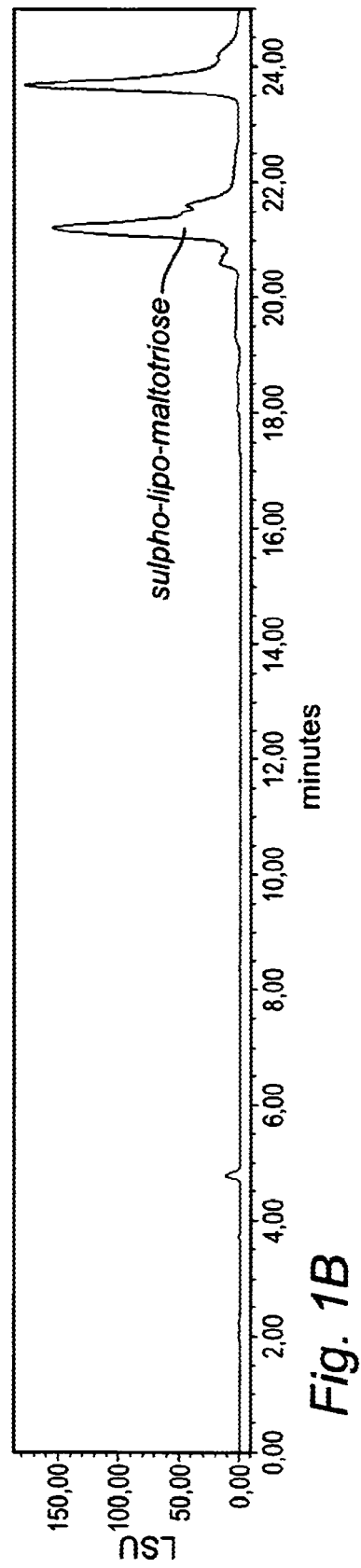

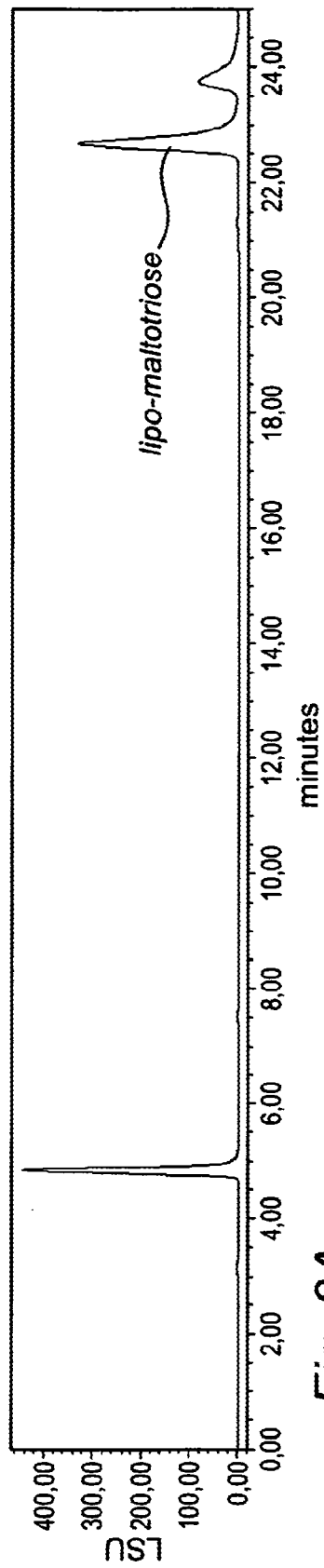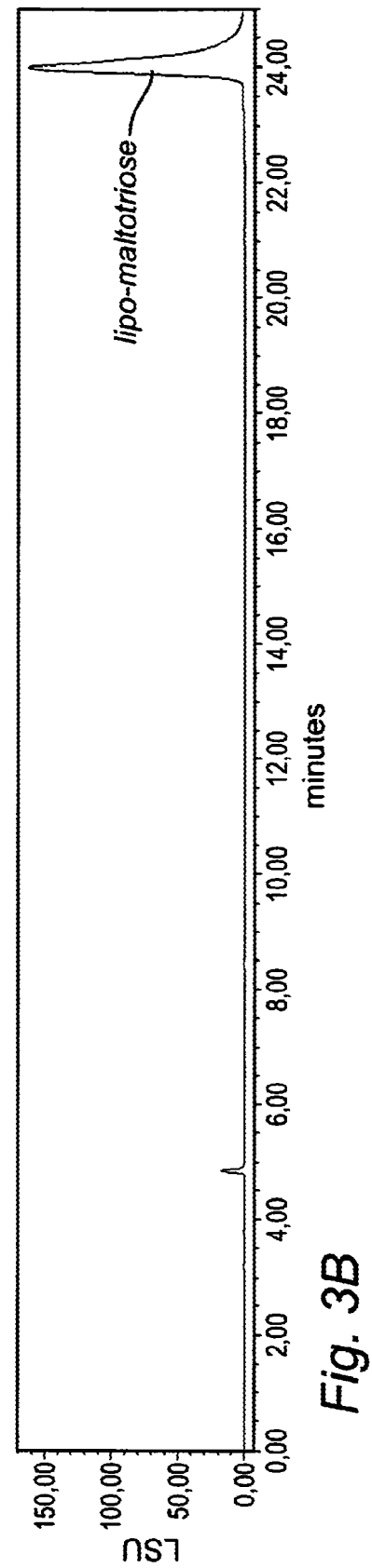

Figure 2:
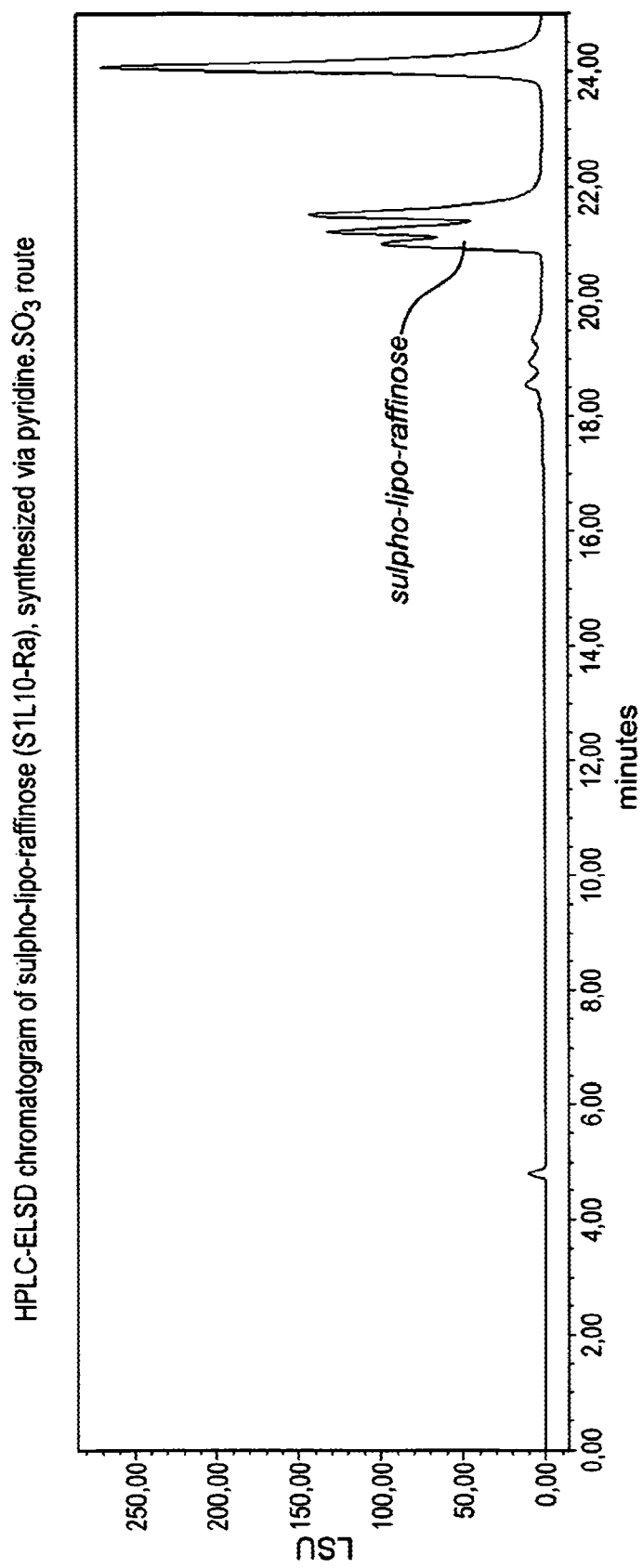

Course of GnRH antibody titer (mean) of rats immunized with GnRH-KLH conjugate in oil-in-water emulsion containing: A) sulpho-lipo-maltotriose (S1L10-Ma), B) sulpho-lipo-raffinose (S1L10-Ra) and C) saccharide compounds at 0 and 8 mg dose and PBS controls without GnRH-KLH conjugate. Rats were immunized on day 0, 14 and 28.

Serum testosterone (pmol/ml) of rats immunized with GnRH-KLH conjugate in oil-in-water emulsion containing: A) sulpho-lipo-maltotriose (S1L10-Ma), B) sulpho-lipo-raffinose (S1L10-Ra) and C) saccharide compounds at 0 and 8 mg dose and PBS controls without GnRH-KLH conjugate. Rats were immunized on day 0, 14 and 28.

Mean body temperature of rats (mean value of 5 rats and 3 immunizations) as change from values measured just before immunization (-2h). Body temperature was measured at 3 hours after immunization and 21 and 45 hours.
Graphs show MBT of rats immunized with GnRH-KLH conjugate in oil-in-water emulsion containing: A) sulpho-lipo-maltotriose (S1L10-Ma), B) sulpho-lipo-raffinose (S1L10-Ra) and C) saccharide compounds at 0 and 8 mg dose and PBS controls without GnRH-KLH conjugate.

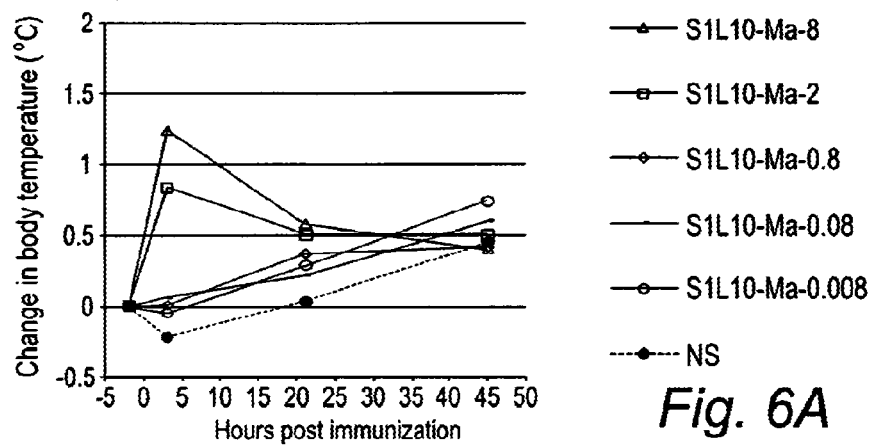

Fig. 6A

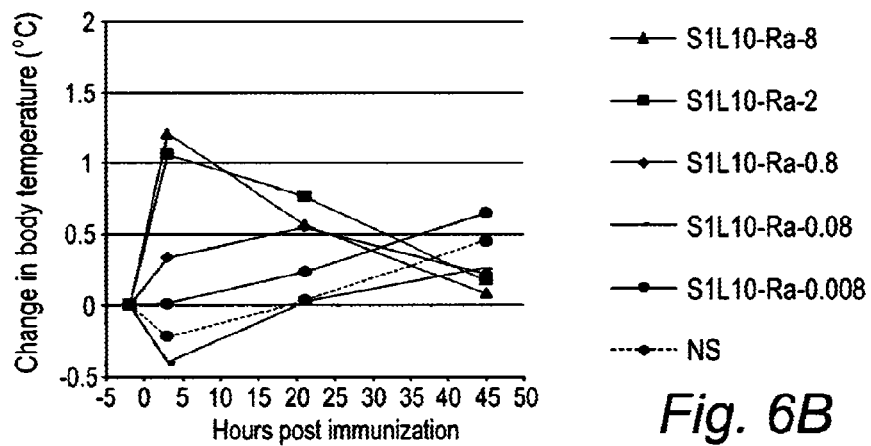

Fig. 6B

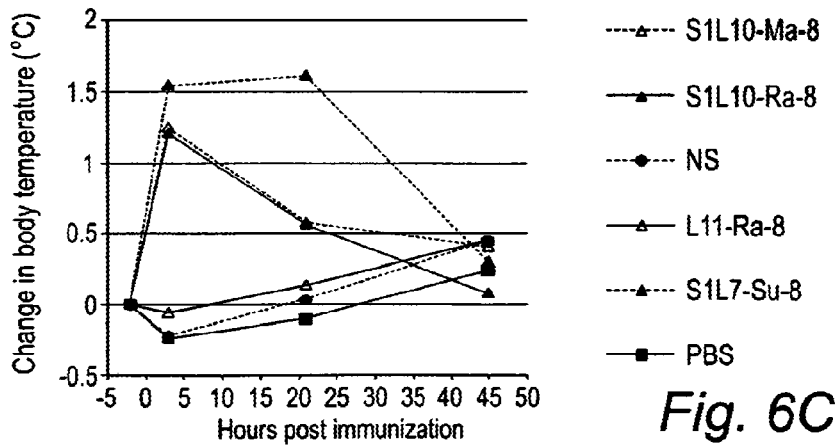

Fig. 6C

Injection site reaction after immunization, cumulative size of injection sites per rat in mm as described in Materials and methods, averaged per treatment group and depicted as mean of 3 subsequent immunizations (day 0, 14 and 28).
Injection site reactions of rats immunized with GnRH-KLH conjugate in oil-in-water emulsion containing: A) sulpho-lipo-maltotriose (S1L10-Ma), B) sulpho-lipo-raffinose (S1L10-Ra) and C) saccharide compounds at 0 and 8 mg dose and PBS controls without GnRH-KLH conjugate.

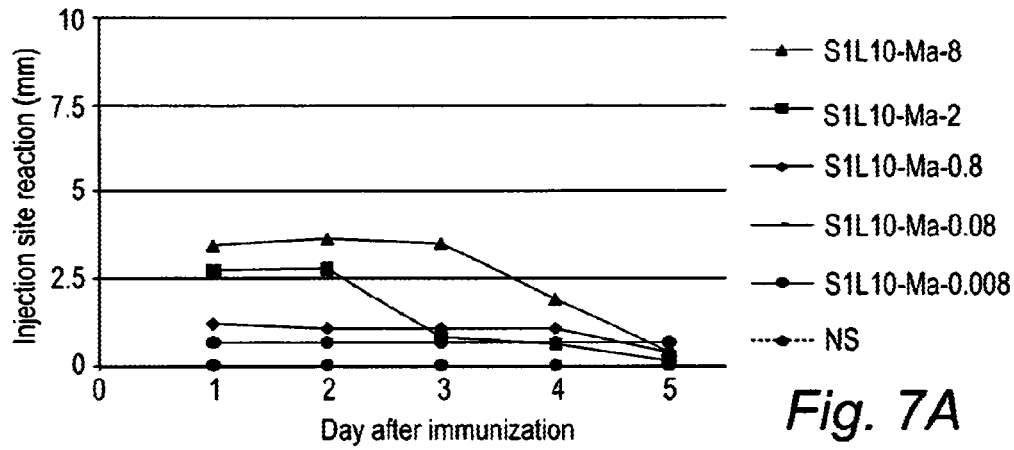

*Fig. 7A*

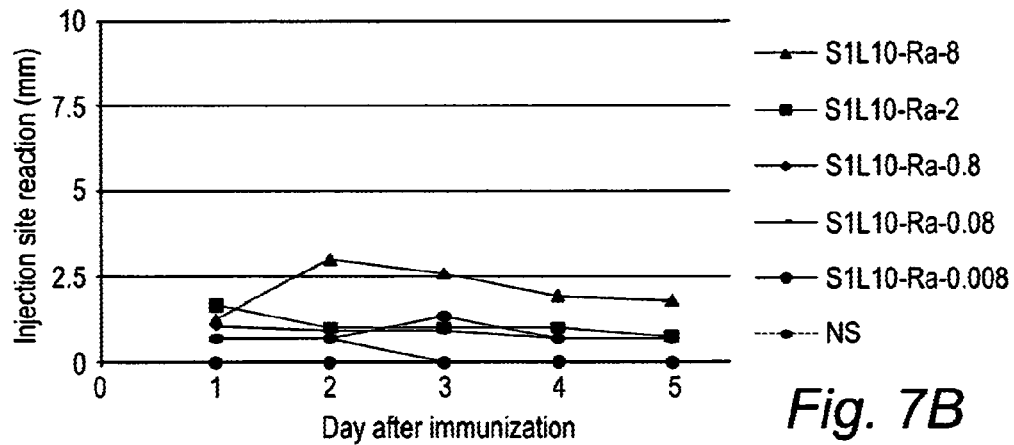

*Fig. 7B*

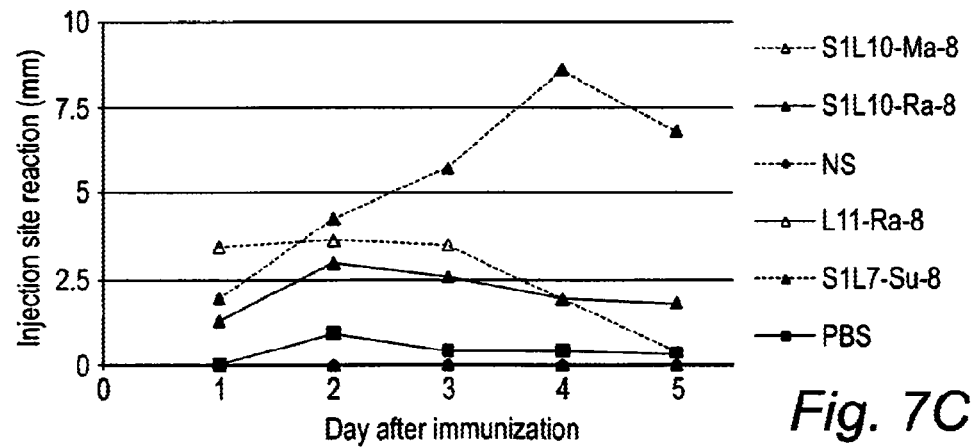

*Fig. 7C*

TRISACCHARIDE DERIVATES, AND THEIR USE AS ADJUVANTS

FIELD OF THE INVENTION

The present invention relates to novel trisaccharide derivates and their use as adjuvants, which trisaccharide derivates comprise a substituted trisaccharide core, which trisaccharide core is fully substituted with fatty acid ester groups, and optionally one or more anionic groups, the invention further relates to a method for preparing these trisaccharide derivates, to trisaccharides obtainable by this method, and to the use of the adjuvant in a vaccine.

BACKGROUND OF THE INVENTION

Antibodies are substances contained in the blood and other fluids of the body, as well as in the tissues, and which bind to antigen to make it innocuous. Antibodies constitute one of the natural defense mechanisms of the body. They are highly specific and they kill, bind or make innocuous the antigen which induced their formation.

The antigen in contact with the immune system, thus activates a complex series of cellular interactions to eliminate the antigen and/or to re-establish the preceding equilibrium.

Two of the characteristic features of antigens are their immunogenicity, that is their capacity to induce an immune response in vivo (including the formation of specific antibodies), and their antigenicity, that is their capacity to be selectively recognized by the antibodies whose origins are the antigens.

It is known how to stimulate the immune response deliberately by administering a specific antigen by means of a vaccine. The procedure allows the retention of a state of immune response in the organism which allows a more rapid and more effective response of the organism during subsequent contact with the antigen.

However, some antigens have only a weak immunogenicity and they induce an insufficient immune response to produce an effective protection for the organism. This immunogenicity can significantly be improved if an antigen is co-administered with an adjuvant.

Adjuvants are substances that enhance the immune response to antigens, but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Adjuvants have been used for many years to improve the host immune response to, for example, vaccines. Intrinsic adjuvants are normally the components of the killed or attenuated bacteria used as vaccines. Extrinsic adjuvants are immunomodulators which are typically non-covalently linked to antigens and are formulated to enhance the host immune response.

Aluminium hydroxide and aluminium phosphate (collectively referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum.

A wide range of extrinsic adjuvants can provoke immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP).

Chemically defined adjuvants, such as monophosphoryl lipid A, phospholipid conjungates have been investigated (see Goodman-Snitkoff et al., J. Immunol. 147:410-415 (1991) as has encapsulation of the protein with a proteoliposome (see Miller et al., J. Exp. Med. 176:1739-1744 (1992)).

Synthetic polymers have also been evaluated as adjuvants. These include the homo- and copolymers of lactic and glycolic acid, which have been used to produce microspheres that encapsulate antigens (see Eldridge et al., Mol. Immunol. 28:287-294 (1993)).

Nonionic block copolymers are another synthetic adjuvant being evaluated. Adjuvant effects have also been investigated for low molecular weight copolymers in oil-based emulsions (see Hunter et al., The Theory and Partical Application of Adjuvants (Ed. Stewart-Tull, D.E.S.) John Wiley and Sons, NY. Pp. 51-94 (1995)) and for high molecular weight copolymers in aqueous formulations (Todd et al., Vaccine 15:564-570 (1997)).

Desirable characteristics of ideal adjuvants are lack of toxicity and an ability to stimulate a long lasting immune response. One of the most commonly used adjuvants in humans is alum. Other adjuvants, such as Saponin, Quil A and the water in oil adjuvant, Freund's with killed tubercle bacilli (Freund's complete) or without bacilli (Freud's incomplete), have had limited use in humans due to their toxic effects; and concerns have been raised as to undesirable effects in animals.

Simply said, many adjuvant formulations have been described but most are never accepted for routine vaccines, and few have been approved for use in humans. This is mainly due to their toxicity. For example, the mineral oils used as adjuvants in certain animal vaccines are not readily degraded and persist at the site of injection thereby causing unacceptable granulomas; and, in general adjuvant formulations such as mineral compounds oil emulsions, liposomes and biodegradable polymer microspheres cause local reactions due to depot formation at the site of injection.

Examples of adjuvants presently approved in human vaccines include Alum, MF59 (an oil in water emulsion), MPL (a glycolipid), VLR, Immunopotentiating Reconstituted Influenza Virosomes (IRIV) and cholera toxin (see Reed et al. Trends in Immunology 30:23-32 (2008).

One group of adjuvants known in the art are the so called sulpholipopolysaccharides, i.e. polysaccharides containing both fatty acid esters and sulphate esters (Hilgers et al., Immunology 60, pp. 141-146, 1986). A method for preparing these compounds has been described in the international patent application WO96/20222 and WO 96/20008. These methods for preparing sulpholipopolysaccharides result in the formation of different sulpholipopolysaccharides derivates varying in the number of fatty acids esters present per polysaccharide molecule, the number of sulphate esters present per polysaccharide molecule, the number of hydroxyl groups per polysaccharide molecule and the distribution of the fatty acid esters, the sulphate esters and the hydroxyl groups over the polysaccharide molecule. This means that during preparation of these sulpholipopolysaccharides a mixture is obtained of many different sulpholipopolysaccharides. Consequently, the yield of the desired sulpholipopolysaccharide is relatively low or the adjuvant needs to be used as a difficult to characterise mixture causing regulatory issues.

In the European patent EP 1233969 an adjuvant composition is claimed which adjuvant comprises sulpholipodisaccharides. Also a method is described for preparing these sulpholipodisaccharides. In one of the embodiments the sulpholipodisaccharides prepared are fully substituted with fatty acid ester or sulphate ester groups. However, as will be further described in the following, when these sulpholipodisaccharides are used as adjuvants in animals, undesired side effects such as occurrence of mean body temperature rise (including fever) and local irritation (tissue swelling) occur.

DETAILED DESCRIPTION OF THE INVENTION

In view of the foregoing it is an object of the present invention to provide compounds which are relatively easy and inexpensive to prepare, have good adjuvating properties and induce a minimum of undesired side effects when used clinically. It is a further object of the present invention to provide compounds that can be used in an adjuvant composition, for example in combination with a vaccine, which compounds have an excellent safety and side effect profile.

A first and second aspect of the present invention relates to trisaccharide derivates and their use as an adjuvant. The trisaccharide derivates according to the present invention comprise a substituted trisaccharide core, which trisaccharide core is fully substituted with fatty acid ester groups, and optionally one or more anionic groups.

The trisaccharide derivates according to the present invention are highly suitable for use as adjuvant for vaccines. They have a side effect profile which is surprisingly significantly better than the side effect profile of other adjuvants which are based on polysaccharide derivates, such as for example adjuvants based on disaccharides. Animals which have been vaccinated with an antigen composition and an adjuvant composition comprising the trisaccharide derivates according to the invention show less increase in mean body temperature compared with for example the disaccharide derivates of EP 1233969. Also the occurrence of local reactions (tissue swelling) around the area of injection is lower when an adjuvant is used which comprises the trisaccharide derivates according the invention.

The term antigen as used herein, refers to any component or material that induces a immunological reaction in the human or animal body, such as a virus, a bacterium, mycoplasma, a parasite or a tumor cell, a subunit of a micro-organism, such as a protein, polysaccharide, peptide, glycoprotein, polysaccharide-protein conjugate, peptide-protein-conjugate.

The antigen can for example consist of or contain one or more live organisms, inactivated organisms, or so-called sub-units (the latter e.g. prepared synthetically, or by recombinant DNA methods, or isolated from the organisms). The term antigen further refers to any component that can induce an immune reaction in the human or animal body.

The trisaccharide core of the derivates of the present invention is preferably derived from raffinose, melezitose, maltotriose, nigerotriose, maltotriulose or kestose. It is particularly preferred that the trisaccharide core is derived from raffinose, melezitose or maltotriose, most preferably raffinose or maltotriose. These trisaccharides have in their normal. i.e. unsubstituted form eleven OH-groups which are available for reactions such as for example esterificaction with fatty acids. However, it is also possible that one or more, preferably one, of the OH-groups has reacted with an anionic group, such that for example a sulphate ester or phosphate ester group is obtained, preferably a sulphate ester group is obtained.

In a preferred embodiment of the present invention the trisaccharide derivates according to the invention comprises no anionic groups but only fatty acids groups, preferably identical fatty acid groups.

According to another preferred embodiment the trisaccharide derivates according to the invention comprise one or two anionic groups with ten or nine fatty acid groups, respectively, per substituted trisaccharide core. Preferably the fatty acid groups are identical.

The term anionic group as used herein refers to a negatively charged moiety (i.e. negatively charged at neutral pH or the pH of the environment in which the derivate is applied). Such an anionic group may for example be a sulphate, a sulphonate or a phosphate. Preferred anionic groups include sulphate ester groups or phosphate ester groups. Examples of such groups are —O—SO$_2$—ONa or —O—SO$_2$—ONH$_4$, —O—SO$_2$-OTEA (i.e. sulphate triethylammonium).

In a preferred embodiment of the present invention the fatty acid ester group which is covalently bound to the substituted trisaccharide core is an ester of a straight, branched, saturated or unsaturated fatty acid with a chain length of 4 to 20 carbon atoms, preferably 6 to 18, more preferably 8 to 16 carbon atoms, most preferably 10-14 and highly preferred 12 carbon atoms.

Although it is within the scope of the present invention that the substituted trisaccharide core is substituted with more than one type of fatty acid ester, it is preferred that only one type is used, i.e. that all fatty acid esters are identical.

The use of fatty acids is highly preferred, however it is also envisaged by the present invention that other carboxylic acids, preferably closely related to fatty acids, may provide favourable results.

Preferably, the fatty acid ester is the ester of saturated fatty acids, monounsaturated fatty acids or polyunsaturated fatty acids, such as butyric acid, caproic acid, caprylic acid, capric acid, lauric acid, myristic acid, palmitic acid, palmitoleic acid, stearic acid, ricinoleic acid, vaccenic acid, arachidic acid, gadoleic acid, arachidonic acid, oleic acid or linoleic acid. Most preferably lauric acid.

In a preferred embodiment the substituted trisaccharide core is derived from raffinose, melezitose or maltotriose and is the trisaccharide derivate fully substituted with identical fatty acid ester groups per substituted trisaccharide, i.e. the trisaccharide core is substituted with eleven identical fatty acid ester groups.

In another preferred embodiment the substituted trisaccharide core is derived from raffinose, melezitose or maltotriose and comprises one or two anionic groups, such as a sulphate ester or a phosphate ester group, and ten or nine, respectively, identical fatty acid ester groups per substituted trisaccharide. Most preferably the fatty acid ester is the ester of lauric acid.

A third aspect of the present invention relates to a method for preparing a trisaccharide derivate comprising the steps of:
i) providing a trisaccharide and dissolving it in a solvent; and
ii) esterifying all OH-groups of the trisaccharide with a fatty acid, or source thereof, optionally reacting at least one of the OH-groups of the trisaccharide with an anionic agent.

Due to the fact that all the OH-groups are reacted with anionic groups and/or fatty acids, few impurities are being formed. This means that it is possible to obtain without extensive purification steps a pharmaceutically acceptable pure form of an envisaged trisaccharide derivate. If only one kind of fatty acid is used, such as lauric acid, even less purification is needed to obtain the desired trisaccharide derivate in a pharmaceutically acceptable pure form. Another advantage of the method of the present invention is that the desired trisaccharide derivates are easily obtained in relatively large quantities, making the method economically attractive.

In a preferred embodiment of the present invention the trisaccharide derivates prepared comprise no anionic groups but only fatty acids groups, preferably identical fatty acid groups, i.e. all OH-groups have reacted with a fatty acid or source thereof.

According to another preferred embodiment the trisaccharide derivates prepared comprise one or two anionic groups with ten or nine fatty acid groups, respectively, per substituted trisaccharide core. Preferably the fatty acid groups are identical.

The trisaccharides used in the above mentioned method are preferably raffinose, melezitose, maltotriose, nigerotriose, maltotriulose or kestose. More preferably, raffinose, melezitose or maltotriose are used, most preferably maltotriose or raffinose.

The meaning of fatty acids as used in the above mentioned method refers to any source of fatty acids, including fatty acid salts, fatty acids halides, fatty acid esters and derivates. Preferably the fatty acids used in the claimed method are straight, branched, saturated or unsaturated fatty acids with a chain length of between 4 to 20 carbon atoms, preferably between 6 to 18, more preferably from 8 to 16 carbon atoms, most preferably 10 to 14 carbon atoms, highly preferred 12 carbon atoms.

Preferably, the fatty acids used are saturated fatty acids, monounsaturated fatty acids or polyunsaturated fatty acids, such as butyric acid, caproic acid, caprylic acid, capric acid, lauric acid, myristic acid, palmitic acid, palmitoleic acid, stearic acid, ricinoleic acid, vaccenic acid, arachidic acid, gadoleic acid, arachidonic acid, oleic acid or linoleic acid. Most preferably lauric acid.

As mentioned above, in a preferred embodiment of the present invention at least one of the OH groups is reacted with an anionic reagent. Preferably, the anionic agent used is a sulphating or phosphating agent such as gaseous $SO_3$, $HCLSO_3$, $SO_3$.pyridine, $SO_3$-2-methylpyridine, $SO_3$-2,6-dimethylpyridine, $SO_3$-dimethylformamide, $SO_3$-trimethylamide, $SO_3$-triethylamine, $SO_3$-dimethylanaline, $SO_3$—N-ethylmorpholine, $SO_3$-diethylalanine, $SO_3$-dioxane and combinations thereof. Most preferably the sulphonating agent is $SO_3$.pyridine or $SO_3$.triethylamine.

The most preferred sulphating agent is $SO_3$.pyridine. It is further preferred that reacting at least one of the OH-groups of the trisaccharide with a sulphating agent is carried out before the esterification of the trisaccharide with a fatty acid. The advantage of first carrying out the reaction with a sulphating agent is that the sulphating agent reacts first with the so called primary OH-groups before reacting with other OH groups, thereby reducing the number of isomers formed.

In a preferred embodiment the ratio trisaccharide:anionic agent:fatty acid equivalents is 1:0-3:8-11, preferably 1:0-1:10-11. Within these claimed ranges the complete substitution of the OH-groups of the trisaccharide with fatty acid esters and optionally the anionic group, such as a sulphate ester, is efficiently obtained.

Preferably, the solvent used for carrying out the reaction is a mixture of pyridine and dimethylformamide.

In an additional step of the present method the trisaccharide derivates are subjected to an additional step of mixing them with a pharmaceutically acceptable excipient or diluent, such that an adjuvant composition is obtained.

A fourth aspect of the present invention relates to adjuvant compositions comprising trisaccharide derivates according to the invention, or a mixture thereof. When such trisaccharide derivates are formulated into an adjuvant composition they are preferably mixed with pharmaceutically acceptable excipients or diluents. Preferably the adjuvant composition is formulated as an oil in water emulsion. Suitable oils to be used are amongst others animal oils, vegetable oils and mineral oils, such as fish oil, vitamin E, squalane, squalene. Preferably, use is made of squalane, preferably in combination with polysorbate.

Although it is possible to only use one kind of trisaccharide derivate it is also within the scope of the invention to use in the adjuvant composition a mixture of different trisaccharide derivates according to the invention. In a preferred embodiment a mixture is used of trisaccharide derivates according to the invention with an anionic group, such as a sulphate ester group, and the same trisaccharide derivates without an anionic group, e.g. sulpho-lipo-raffinose and lipo-raffinose. Most preferably the fatty acid esters of the trisaccharides derivates used in such a mixture are the same, such as for example the ester of lauric acid.

A fifth aspect of the present invention relates to a vaccine comprising the adjuvant composition, or trisaccharide derivate as mentioned above.

Both the adjuvant composition, antigen composition or vaccine are preferably administered parenterally. Suitable means for parenteral administration include intramuscular, subcutaneous, subdermal and intradermal administration. Suitable devices for parenteral administration include needle (including microneedle) injectors, and transdermal delivery systems.

The parenteral formulation may readily be prepared by someone skilled in the art according to standard methods. Preferably the parenteral formulation is prepared as an oil in water emulsion.

The preparation of parenteral formulations under sterile conditions, for example, by filtration may readily be accomplished using standard pharmaceutical techniques well known to those skilled in the art.

The vaccine or the adjuvant composition according to the invention can be administered to humans and many different target animals, such as for example pigs, cattle, poultry, dogs, cats, horses and the like.

A sixth aspect of the present invention relates to a kit comprising the above mentioned adjuvant composition and an antigen composition.

It may be desirable to administer a combination of the adjuvant composition and antigen composition or vaccine separately. In such a case the adjuvant composition and antigen composition may conveniently be combined in the form of a kit. Such a kit could for example be a two vial system or a dual chamber syringe.

The invention will now be further described by the following, non-limiting examples

EXAMPLES

Preparation of Trisaccharide Derivates According to the Invention

Example 1

General Synthesis of Sulpho-Lipo-Trisaccharides According to the Invention

A trisaccharide is dried in a vacuum oven to remove the crystal water. The trisaccharide (5 g) is subsequently dissolved, under a stream of nitrogen, in 30 mL of DMF and 14 mL of pyridine in a 100 mL three-neck round-bottom flask, equipped with a reflux-condensor. 1.05 equivalent of pyridine.$SO_3$ is added under vigorous stirring. After 1 hr the flask is cooled in ice water and under vigorous stirring lauroyl chloride is added drop-wise to prevent heating of the reaction mixture. After 15 min the ice bath is slowly heated to 40° C. The progress of the reaction is monitored by HPLC. After completion of the reaction the mixture is concentrated in vacuo in a rotary evaporator (heated up to 60° C.). The crude product is taken up in 300 mL heptane and 150 mL brine. The organic layer is separated in a 500 mL reparatory funnel, dried on sodium sulfate and filtered. The heptane solution is concentrated in vacuo. The oil obtained is dissolved in 200 mL heptane and triethylamine (2.37 mL) is added drop wise. The solution obtained is filtered and concentrated in vacuo. The oil is dissolved again in 100 mL heptane, filtered and the solution is concentrated in vacuo.

Example 2

Synthesis of Sulpho-Lipo-Maltotriose (S1L10-Ma) Via Pyridine.SO$_3$ Route

The title product was synthesized following the general method described in Example 1 with the following details: maltotriose (5.1 g, 10 mmol) was dried in a vacuum stove at <10 mbar for 19 hrs at 40° C. and 48 hrs at 70° C., yield 4.9 g. The dried maltotriose was dissolved in 30 mL of DMF and 14 mL of pyridine and sulfated with 1.6 g (1.05 eq) of pyridine.SO$_3$, suspended in 2 mL of DMF. After 1 hr the sulfo-trisaccharide was esterified in an ice bath with 11 equivalents (25.5 mL) of lauroyl chloride. The mixture was slowly heated to 40° C. and reacted for 3 hrs. Reaction steps were followed by HPLC-ELSD. The product was isolated after extraction and triethylamine exchange. Yield of the thick brown-yellow syrup: 15.5 g+5.5 g (second crop from evaporation flask after heating to 50° C.). HPLC-ELSD chromatogram: see FIG. 1A.

Example 3

Alternative Synthesis of Sulpho-Lipo-Maltotriose (S1L10-Ma) Via Pyridine.SO$_3$ Route The title product was synthesized following the general method described in Example 1 with the following details: maltotriose (5.0 g, 10 mmol) was dried in a vacuum stove at <10 mbar for 20 hrs at 40° C. and 90 hrs at 70° C., yield 4.9 g. The dried maltotriose was dissolved in 30 mL of DMF and 1.6 g (1.05 eq) of pyridine.SO$_3$ was added as a suspension in 14 mL of pyridine. After 1 hr the sulpho-trisaccharide was esterified in an ice bath with 11 equivalents (25.2 mL) of lauroyl chloride and was slowly heated to 40° C. Samples for HPLC-ELSD analysis were taken at regular time points in the process. The reaction with lauroyl chloride was left overnight at ambient temperature Work up was done as described in example 1. Yield of the thick brown-yellow syrup: 24.7 g. HPLC-ELSD chromatogram: see FIG. 1B.

Example 4

Synthesis of Sulpho-Lipo-Raffinose (S1L10-Ra) Via Pyridine.SO$_3$ Route

The title product was synthesized as described in example 1 with the following details: raffinose pentahydrate (5.0 g, 10 mmol) was dried in a vacuum stove at <10 mbar for 24 hrs at 30° C. and 90 hrs at 60° C., yield 4.3 g. The dried raffinose was dissolved in 30 mL of DMF and 14 mL of pyridine. Pyridine.SO$_3$ (1.6 g, 1.05 eq) was added in one batch. After 1 hr the sulpho-trisaccharide was esterified in an ice bath with 12 equivalents (23.5 mL) of lauroyl chloride and was slowly heated to 40° C. After 4 hrs, the mixture was concentrated in vacuo, extracted and treated with TEA as described in example 1. Yield of the thick yellow-brown syrup: 18.0 g. HPLC-ELSD chromatogram: see FIG. 2.

Example 5

Synthesis of Lipo-Maltotriose (L11-Ma)

The title product was synthesized following the general method described in Example 1 with the following details: Maltotriose hydrate (0.50 g) was dried in a vacuum oven. The dried trisaccharide (0.49 g, 0.97 mmol) was dissolved in pyridine (1.4 mL) and DMF (3 mL), cooled in an ice bath and reacted with lauroyl chloride (3.36 mL, 15 eq) for 1 hrs at 0° C., followed by 16 hrs at room temperature. The reaction mixture became a gel, upon the addition of 3 mL of heptanes and sonification the product dissolved. The addition of heptane was repeated twice. The organic phase (75 mL) was washed with water and a three layer system was formed. Only the organic layer was isolated, dried over sodium sulphate, filtered and concentrated to yield a thick yellow-brown syrup: 1.39 g. HPLC-ELSD chromatogram: see FIG. 3A.

Example 6

Synthesis of Lipo-Raffinose (L11-Ra)

Raffinose pentahydrate (0.50 g) was dried in a vacuum oven. The dried raffinose (0.41 g, 0.86 mmol) in pyridine (1.4 mL) and DMF (3 mL) was cooled in an ice bath and reacted with lauroyl chloride (2.97 ml, 15 eq) for 1 hrs at 0° C., followed by 18 hrs at room temperature. The reaction mixture was diluted with heptane (50 ml) and washed with water (25 ml). The organic phase was dried over sodium sulphate, filtered and concentrated to yield a thick yellow-brown syrup: 2.33 g. HPLC-ELSD chromatogram: see FIG. 3B.

Effect of Adjuvants Comprising the Trisaccharide Derivates According to the Invention on Anti GnRH Titers, Serum Testosterone Levels and Occurrence of Adverse Effects.

Animal experiments have been carried out to assess the efficacy and possible adverse effects associated with the use of the trisaccharides according to the invention as an adjuvant. In this study in rats, three (sulpho-) lipo-trisaccharides based adjuvants were tested: sulpho-lipo-maltotriose (one sulphate-ester group and ten lauroyl ester groups, S1L10-Ma), prepared according to Example 3; sulpho-lipo-raffinose (one sulphate-ester group and ten lauroyl ester groups, S1L10-Ra), prepared according to Example 4; and lipo-raffinose (raffinose fully substituted with lauroyl ester groups, L11-Ra), prepared according to Example 6. The adjuvants comprising sulpho-lipo-maltotriose also comprised lipo-maltotriose (fully substituted with lauroyl ester groups, L11-Ma). The adjuvants comprising sulpho-lipo-raffinose also comprised lipo-raffinose (fully substituted with lauroyl ester groups, L11-Ra).

The sulpho-lipo based adjuvants were tested in different doses varying from 0.008-8 mg per dose. The adjuvants were tested in combination with a GnRH-KLH conjugate with 0.7 μg conjugated GnRH per dose. Adjuvanticity of the adjuvants was compared with the positive control adjuvant, sulpho-lipo-sucrose (disaccharide with one sulphate ester group and seven lauroyl acid ester groups, S1L7-Su) and with negative control adjuvant consisting of an squalane-in-water emulsion without saccharide compound and one group receiving PBS only.

Efficacy was determined by antibody titers and biological effects of the induced antibodies on testosterone levels. In order to determine adverse effects of immunization with the adjuvants, daily clinical observations were made and body temperature and injection site reactions was determined.

Preparation of Adjuvant Emulsions
  Saccharides: Sulpho-lipo-maltotriose (S1L10-Ma)
    Sulpho-lipo-raffinose (S1L10-Ra)
    Lipo-raffinose (L11-Ra)
  Squalane (A&E Connock)
  Polysorbate-80 (Fagron)
  Sterile PBS-wit pH 7.4 (Mediabereiding ASG, Lelystad)
  MilliQ water
  Millex syringe driven filter unit 0.22 μm PES, 33 mm, 4.5 cm² (Millipore)
  Microfluidizer M-110S equipped with interaction chamber type: F20Y
  Microtrac Nanotrac Analyzer System NPA-253
The experimental adjuvants were prepared as follows.

TABLE 1

Composition of the emulsions for the different SLS

| Group | Saccharide | Amount SLS (g) | Squalane (g) | Tween-80 (g) | MilliQ (g) | PBS-wit (g) |
|---|---|---|---|---|---|---|
| 1 | Sulpho-lipo-maltotriose (S1L10-Ma-8) | 1.0018 | 4.0010 | 1.0019 | 0.2507 | 18.7495 |
| 2 | Sulpho-lipo-maltotriose (S1L10-Ma-2) | 0.2497 | 4.0051 | 1.0017 | 1.0007 | 18.7515 |
| 3 | Sulpho-lipo-maltotriose (S1L10-Ma-0.8) | 0.1007 | 4.0025 | 1.0030 | 1.1525 | 18.7524 |
| 4 | Sulpho-lipo-maltotriose (S1L10-Ma-0.08) | 0.0101 | 4.0040 | 1.0010 | 1.2439 | 18.7525 |
| 5 | Sulpho-lipo-maltotriose (S1L10-Ma-0.008) | 0.00225 | 9.0018 | 1.0006 | 1.2706 | 18.75 |
| 6 | Sulpho-lipo-raffinose (S1L10-Ra-8) | 1.0029 | 4.0004 | 1.0009 | 0.2528 | 18.7495 |
| 7 | Sulpho-lipo-raffinose (S1L10-Ra-2) | 0.2503 | 4.0007 | 1.0008 | 1.0015 | 18.7514 |
| 8 | Sulpho-lipo-raffinose (S1L10-Ra-0.8) | 0.1004 | 4.0015 | 1.0020 | 1.1496 | 18.7526 |
| 9 | Sulpho-lipo-raffinose (S1L10-Ra-0.08) | 0.0106 | 4.0003 | 1.0008 | 1.2386 | 18.7529 |
| 10 | Sulpho-lipo-raffinose (S1L10-Ra-0.008) | 0.00154 | 6.1587 | 1.0045 | 1.2526 | 18.76 |
| 11 | None | 0.0000 | 3.9995 | 1.0011 | 1.2527 | 18.74 |
| 12 | Lipo-raffinose (L11-Ra-8) | 1.0006 | 4.0067 | 1.0037 | 0.2502 | 18.76 |

Note:
for group 5 and 10 the saccharide was dissolved in squalane. Of these solutions 4.0056 g (5) and 4.0006 g (10) was used for further emulsion preparation. The SLS content in the final emulsion was 1 mg/25 ml.

TABLE 2

Experimental design

| Group | Saccharide compound | Adjuvant dose |
|---|---|---|
| 1 | sulpho-lipo-maltotriose (S1L10-Ma-8) | 8 mg |
| 2 | sulpho-lipo-maltotriose (S1L10-Ma-2) | 2 mg |
| 3 | sulpho-lipo-maltotriose (S1L10-Ma-0.8) | 0.8 mg |
| 4 | sulpho-lipo-maltotriose (S1L10-Ma-0.08) | 0.08 mg |
| 5 | sulpho-lipo-maltotriose (S1L10-Ma-0.008) | 0.008 mg |
| 6 | sulpho-lipo-raffinose (S1L10-Ra-8) | 8 mg |
| 7 | sulpho-lipo-raffinose (S1L10-Ra-2) | 2 mg |
| 8 | sulpho-lipo-raffinose (S1L10-Ra-0.8) | 0.8 mg |
| 9 | sulpho-lipo-raffinose (S1L10-Ra-0.08) | 0.08 mg |
| 10 | sulpho-lipo-raffinose (S1L10-Ra-0.008) | 0.008 mg |
| 11 | no saccharide (NS) | 0 |
| 12 | lipo-raffinose (L11-Ra) | 8 mg |
| 13 | sulpho-lipo-sucrose (S1L7-Su-8) | 8 mg |
| 14 | PBS control (no antigen, no adjuvant) | 0 |

The oil phase components (Saccharide, squalane, polysorbate-80 and MilliQ water, amounts as indicated in table 1) were weighed in a 50 ml Falcon tube. The components were mixed using a vortex and heated in a water bath at 50° C. until the saccharide was dissolved. The warm oil phase was added to the water phase (PBS) and the two phases were mixed by vortex and ultra-turrax at 24000 min$^{-1}$ for approximately 30 sec with intervals. Subsequently, the emulsion was formed by Microfluidizer processing. The operating pressure was set to 500 kPa (5 bar) and each mixture was passed three times under cooling of the interaction chamber in an ice bath. Each emulsion was subjected to manual sterile filtration. The particle size of the emulsion was measured using a Nanotrac particle sizer.

Vaccines 1-13 were formulated by adding equal volume of adjuvant (comprising the saccharide compounds as shown in table 2) to the water phase (containing 0.7 μg conjugated GnRH). Vaccine 14 consists of PBS only. The following vaccines were prepared:

Animals and Immunization

Male Wistar rats, 10 weeks of age, were housed with 3 rats per cage. Rats had ad libitum access to food en water. Rats were immunized at day 0, 14 and 28, according to the experimental design (Table 2) with 400 μl vaccine comprising 200 μl water phase and 200 μl adjuvant. Two intramuscular injections (100 μl each) were injected at the left and right inner thigh and 2×100 μl was injected subcutaneously in the neck region. Each group consists of 5 rats.

Blood samples for serum were collected from all animals prior to the immunizations and at day 41 and 56

Efficacy of the Vaccines
Assays

GnRH specific antibodies were measured by ELISA. Plates (96 wells) were precoated with 0.2% glutardialdehyde in phosphate buffer (pH 5) for 3 hours at room temperature, washed with 0.1 M phosphate buffer (pH 8) and coated with 100 μl per well of a solution containing 10 μg GnRH (Pepscan Presto, Lelystad, The Netherlands) per ml phosphate buffer (pH 8) and incubated for 3 hours at 37° C. Coated plates were washed with 0.05% Tween-80. Serum samples were diluted (1/10) in PEM (1% Tween-80 with 4% horse serum). This dilution was further diluted in the 96-well plate (100 μl per well, 8 steps) and incubated 1 hour at 37° C. After washing with 0.05% Tween-80, 100 μl of goat-anti-rat antiserum conjugated with peroxidase in PEM was added to the wells. Plates were incubated for 1 h at 37° C. and washed 12 times with 0.05% Tween-80. Subsequently, 150 μl of a substrate solution containing 2,2-azino-bis-(3-benzthiazoline-6-sulphonic acid) (ABTS) plus $H_2O_2$ was added to the wells of the plates. Plates were incubated for 45 minutes at ambient room temperature and absorbance was measured at 405 nm. Antibody titer was expressed as the 10 log of the dilution factor that gives an optical density of 4 times background (approx. 100).

Serum testosterone levels were measured using a commercially available Testosterone EIA (Beckman Coulter, Woerden, The Netherlands) according to the instructions of the manufacturer.

GnRH Antibody Titers

Figure 4A:
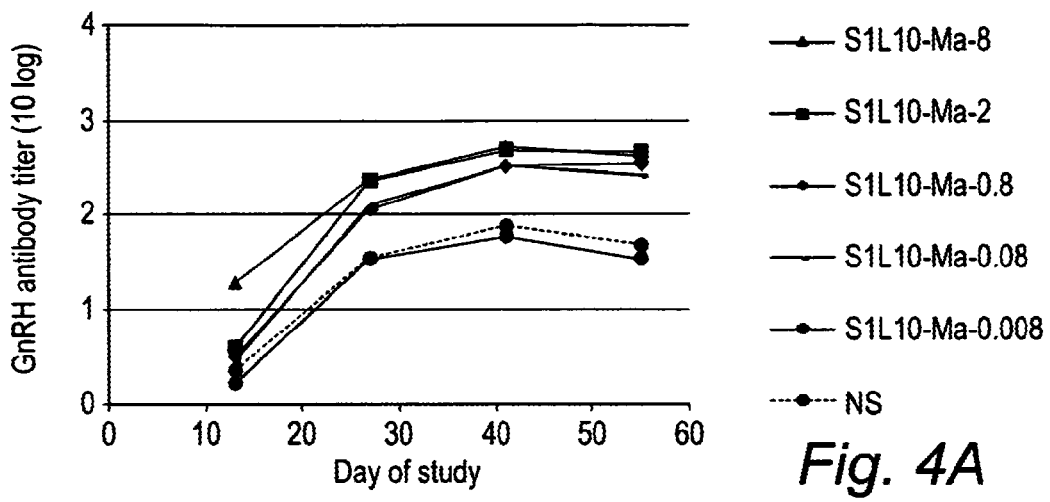
Figure 4B:
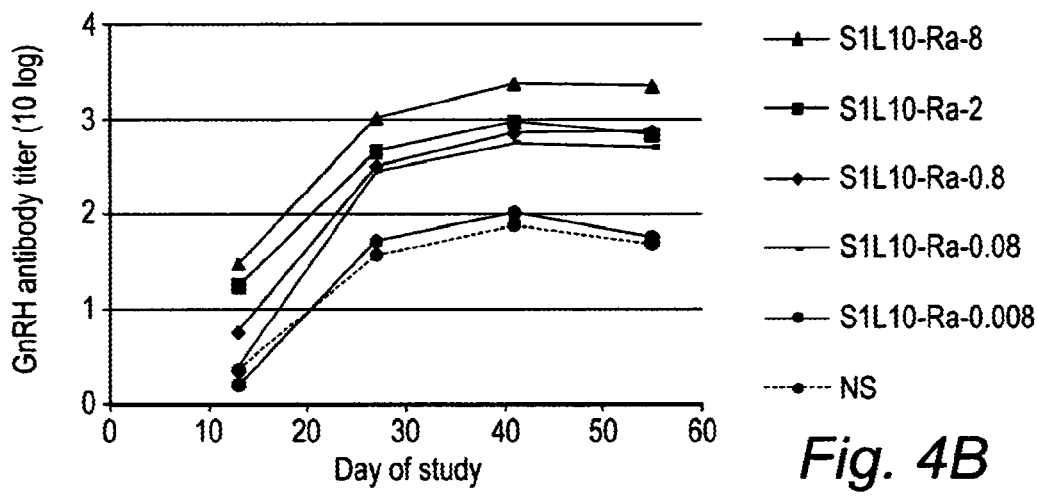

GnRH antibody titers of groups treated with sulpho-lipo-maltotriose (S1L10-Ma) and sulpho-lipo-raffinose (S1L10-Ra) are depicted in FIGS. 4A and 4B. Both sulpho-lipo-trisaccharides induced dose dependent antibody titers against GnRH. Antibody titers were substantially higher for rats treated with 0.08-8 mg sulpho-lipo-trisaccharide than in rats treated with adjuvant without saccharide (NS, group 11), demonstrating the significant contribution of the sulpho-lipo-trisaccharide to the immune response.

Figure 4C:
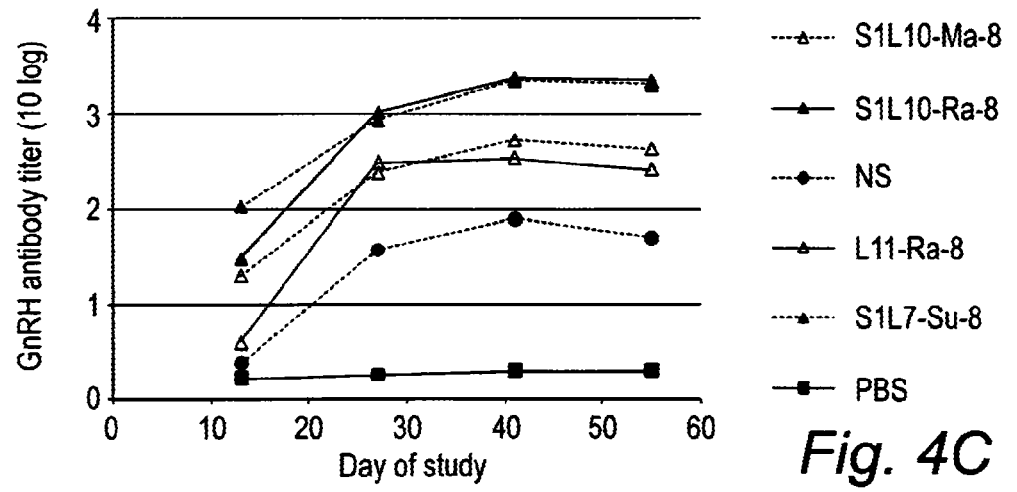

FIG. 4C clearly shows that GnRH antibody titers of rats that received 8 mg saccharide compounds according to the invention, i.e. S1L10-Ma-8, S1L10-Ra-8 and L11-Ra-8 were substantially higher than in rats treated with squalane emulsion only (NS), emphasizing strong adjuvanticity of both S1L10- and L11-trisaccharides.

Serum Testosterone

Figure 5A:
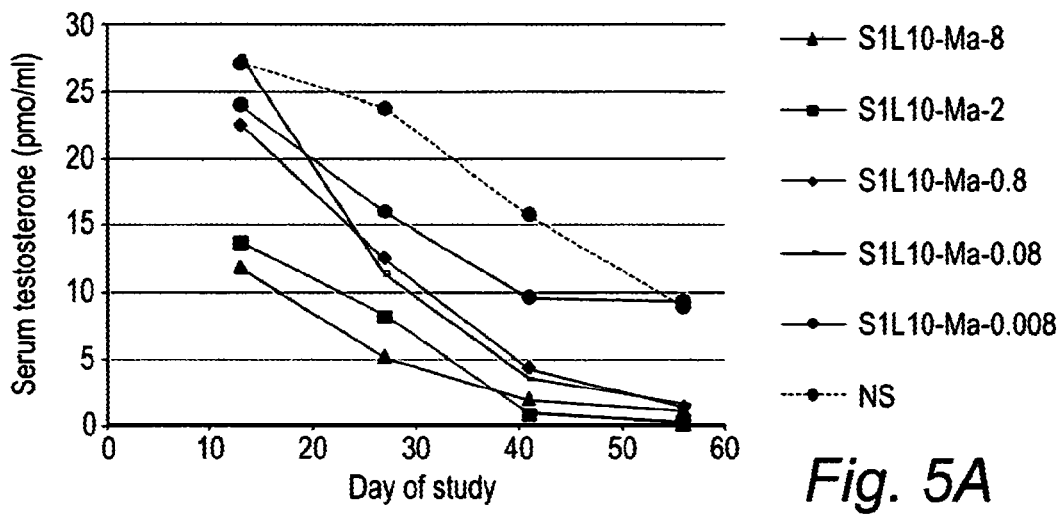
Figure 5B:
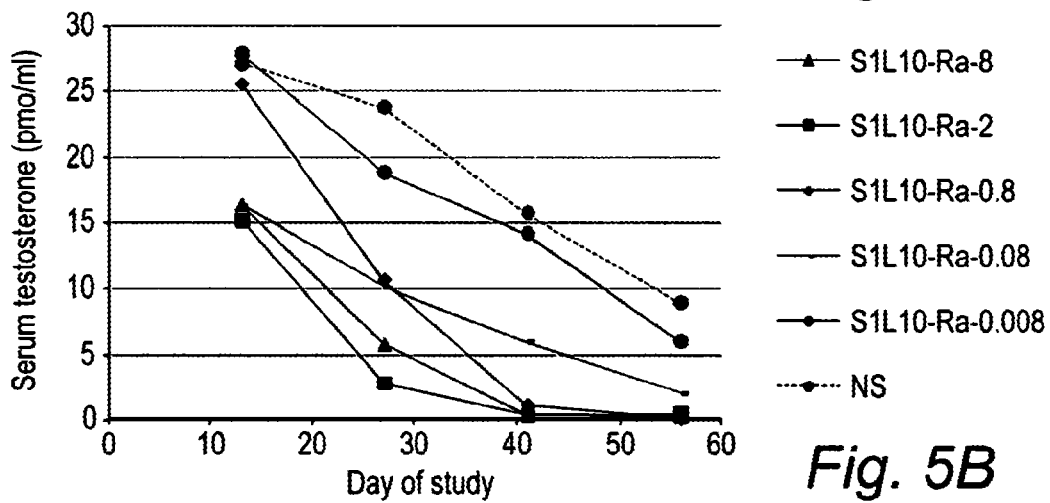
Figure 5C:
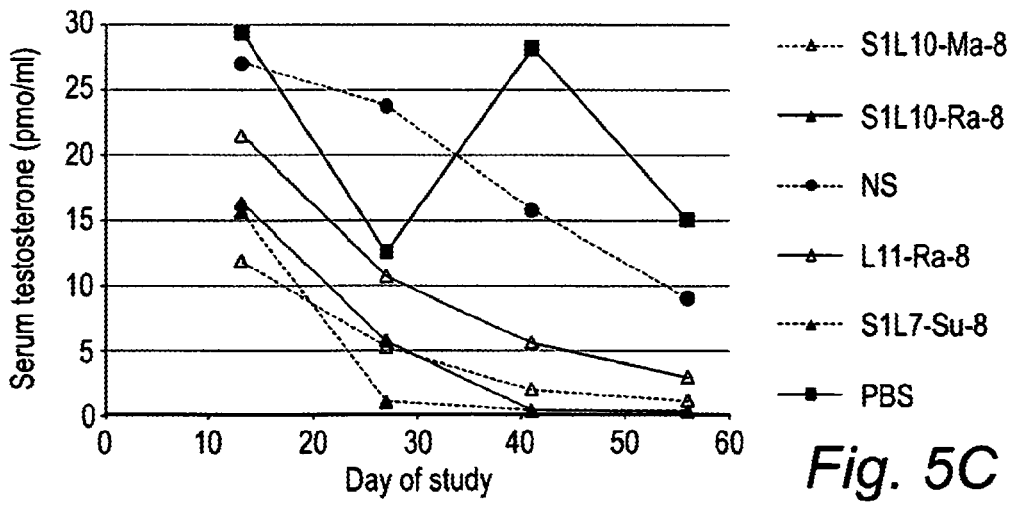

Immunization with GnRH-KLH conjugate emulsified with the adjuvant comprising the sulpho-lipo-trisaccharides according to the invention, i.e. S1L10-Ma and S1L10-Ra, resulted in a dramatic decline of serum testosterone levels from 0.08 mg sulpho-lipo-trisaccharide onwards (FIG. 5 A-B), while the effects of the lowest sulpho-lipo-trisaccharide dose (0.008 mg) on serum testosterone were similar to the oil-in-water emulsion without saccharide compound. Immunization with the lipidated trisaccharide (L11-Ra-8) also induced decreasing testosterone levels (FIG. 5C).

Adverse Effects

Rise of Mean Body Temperature

At least once daily clinical observations were made in all animals. Mean body temperature (MBT) was determined for all animals before and after each immunization by rectal temperature. Mean body temperature per group (MBT) are depicted as to preimmunization levels FIG. 6.

At 3 hours after each vaccination, a slight increase in MBT was observed in rats treated with sulpho-lipo-trisaccharides only at 8 and 2 mg dose, while no effects on MBT were noted at 0.8, 0.08 and 0.008 mg. The next day 21 hours after vaccination however, MBT was dropped to almost normal values again (FIGS. 6A and 6B). In contrast, immunization with the disaccharide compound (S1L7-Su-8) which caused a slightly higher increase in MBT than the trisaccharide compounds at 3 hours post vaccination, did not show a decrease in MBT one day post immunization, MBT was still increased at 21 hours after vaccination (FIG. 6C). The lipidated trisaccharide (L11-Ra-8) did not induce any increase in MBT. From FIG. 6 it is thus clear that the vaccines comprising the compounds according to the invention (S1L10-trisaccharides) as adjuvants induced surprisingly significantly shorter temperature effects when compared to the disaccharide derivates known in the prior art, while the lipidated trisaccharide (L11-trisaccharide) in similarity to the oil-in-water emulsion without a saccharide compound (NS) did not induce any temperature effects at all.

Injection Site Reactions

Before vaccination the injection sites were assessed for the presence of abnormalities or existing local reactions. If such abnormalities or local reactions were absent, the animal was injected on that site. After each immunization, injection sites were inspected for tissue swelling. Size of subcutaneous injection sites was measured (diameter in mm). Since the intramuscular injection site reactions in the hind leg is difficult to determine, only the presence of intramuscular injections sites (tissue swelling) was determined and expressed in arbitrary values (present=10 mm, not present=0 mm) Scores of injection site reactions were added up per rat for the four injection sites at each inspection, means per group were calculated The results thereof are presented in FIG. 7.

After immunization, minor dose dependent injection site reactions were observed in rats treated with sulpho-lipo-trisaccharides, mainly in rats treated with 8 and/or 2 mg (FIGS. 7A and 7B). Size of the injection site reactions gradually decreased at day 3 after immunization and were almost undetectable at day 5 after the subsequent immunization. Injection site reactions caused by immunization with sulpho-lipo-disaccharide (S1L7-Su-8) showed a completely different pattern: Injections site reactions increased in size up to day 4 and were more than 4 times bigger than sulpho-lipo-trisaccharides (see FIG. 7C), moreover at the final inspection 5 days after immunization still significant injection site reactions were present.

The lipidated trisaccharide (L11-Ra-8) did not induce any adverse effects at the site of injection. Clearly, sulpho-lipo-disaccharide comprising vaccine formulations induced more injection site reactions than vaccines comprising sulpho-lipo-trisaccharides according to the invention.

FIGURES

FIG. 1 A-B: HPLC-ELSD chromatogram of sulpho-lipo-maltotriose, synthesized via pyridine.$SO_3$ route FIG. 2: HPLC-ELSD chromatogram of sulpho-lipo-raffinose, synthesized via pyridine.$SO_3$ route FIG. 3 A-B: HPLC-ELSD chromatogram of lipo-maltotriose and lipo-raffinose FIG. 4 A-C: GnRH antibody titer (mean) of rats immunized with various vaccine formulations FIG. 5 A-C: Serum testosterone levels of rats immunized with various vaccine formulations FIG. 6: Mean body temperature of rats immunized with various vaccines formulations FIG. 7: Injection site reaction of rats immunized with various vaccine formulations

The invention claimed is:

1. An adjuvant composition comprising:
   a. a substituted trisaccharide derivate as the adjuvant, wherein the core of the derivate is derived from raffinose, melezitose, or maltotriose and wherein the core is fully substituted with one sulphate ester or phosphate ester group and ten identical fatty acid ester groups; or with two sulphate or phosphate ester groups and nine identical fatty acid ester groups; and
   b. at least one of a pharmaceutical acceptable excipient and diluent.

2. The adjuvant composition according to claim 1, wherein the fatty acid ester groups are esters of a straight, branched, saturated or unsaturated fatty acid with a chain length of 4 to 20 carbon atoms.

3. The adjuvant composition according to claim 1, wherein the fatty acid ester groups are the esters of lauric acid, myristic acid, palmitic acid, stearic acid or arachidic acid.

4. The adjuvant composition according to claim 1, wherein the fatty acid ester groups are the esters of lauric acid.

5. The composition according to claim 1, wherein the core is raffinose.

6. The composition according to claim 1, wherein the core is melezitose.

7. The composition according to claim 1, wherein the core is maltotriose.

8. A vaccine formulation comprising an adjuvant composition according to claim 1.

9. A kit comprising:
an antigen composition; and
an adjuvant composition according to claim 1.

10. A trisaccharide derivate, wherein the core of the derivate is derived from raffinose, melezitose, or maltotriose and wherein the core is fully substituted with one sulphate ester or phosphate ester group and ten identical fatty acid ester groups; or with two sulphate or phosphate ester groups and nine identical fatty acid ester groups, wherein the fatty acid ester groups are esters of a straight, branched, saturated or unsaturated fatty acid with a chain length of 4 to 20 carbon atoms.

11. The trisaccharide derivate according to claim 10, wherein the fatty acid esters are the esters of lauric acid, myristic acid, palmitic acid, stearic acid or arachidic acid.

12. The derivate according to claim 10, wherein the derivate is derived from raffinose.

13. The derivate according to claim 10, wherein the derivate is derived from melezitose.

14. The derivate according to claim 10, wherein the derivate is derived from maltotriose.

15. A method for preparing the trisaccharide derivate according to claim 10, comprising the steps of:
i) providing a trisaccharide and dissolving it in a solvent, wherein the trisaccharide is raffinose, melezitose, or maltotriose; and
ii) esterifying at least one of the OH-groups with a sulphating or phosphating agent and esterifying the other OH groups with a fatty acid, or source thereof,
wherein the fatty acid is a straight, branched, saturated or unsaturated fatty acid with a chain length of 4 to 20 carbon atoms.

16. The trisaccharide derivate according to claim 10, wherein the fatty acid esters are the esters of lauric acid.

17. The method of claim 15, wherein esterifying with the sulphating or phosphating agent is performed before esterifying with the fatty acid, or source thereof.

18. The method according to claim 15, wherein the trisaccharide is raffinose.

19. The method according to claim 15, wherein the trisaccharide is melezitose.

20. The method according to claim 15, wherein the trisaccharide is maltotriose.

* * * * *